| United States Patent [19] | [11] 4,031,074 |
| --- | --- |
| deJongh et al. | [45] June 21, 1977 |

[54] PROCESS FOR THE PREPARATION OF 11β-HYDROXY-18-ALKYL-ESTRANE COMPOUNDS

[75] Inventors: Hendrik Paul deJongh, Oss; Cornelis Wilhelmus van Bokhoven, Berlicum, both of Netherlands

[73] Assignee: Akzona Incorporated, Asheville, N.C.

[22] Filed: July 18, 1975

[21] Appl. No.: 597,271

[30] Foreign Application Priority Data

Sept. 2, 1974 Netherlands .................... 7411607

[52] U.S. Cl. .............. 260/239.55 C; 260/239.57; 260/397.45; 195/51 S
[51] Int. Cl.$^2$ ................ C07J 71/00; C07J 5/00
[58] Field of Search .................... 260/239.55 C; /Machine Searched Steroids

[56] References Cited

UNITED STATES PATENTS 3,780,026  12/1973  Kondo et al. ............. 260/239.55 R Primary Examiner—Elbert L. Roberts
Attorney, Agent, or Firm—Francis W. Young; Hugo E. Weisberger

[57] ABSTRACT

The present invention relates to a novel process for the preparation of 11β-hydroxy-18-alkyl-estrane compounds by reacting an 11β-hydroxy-13-methyl-gonane compound with an excess of an acylhypoiodite to give an estrano-18,11β-lactone, reacting the latter compound with a Grignard compound or an alkyl lithium compound, possibly after hydrolysis of the lactone, and reducing the thus-obtained 11β-hydroxy-18-alkyl-18-ketone to the corresponding 11β-hydroxy-18-alkyl-estrane compound, and to novel intermediates of the subject compounds.

34 Claims, No Drawings

PROCESS FOR THE PREPARATION OF 11β-HYDROXY-18-ALKYL-ESTRANE COMPOUNDS

The invention relates to a novel process for the preparation of 11β-hydroxy-18-alkyl-estrane compounds and novel intermediates thereof.

18-Alkyl-estrane compounds are pharmacologically important 19-nor-steroids. An example of such a compound is norgestrel (= 17α-ethynyl-17β-hydroxy-18-methyl-Δ⁴-estren-3-one), which has found application as an oral progestative and is used i.a. as progestational constituent in contraceptives. In literature many 18-alkyl-estrane compounds with various hormonomimetic properties are described. These compounds usually have a stronger activity than the corresponding 13-methyl compounds.

The natural steroid hormones possess a methyl group in the 13-position. It is only by way of exception that this methyl group is substituted, such as in aldosterone. Most synthetic 19-nor-steroids that have found therapeutic application, are prepared on an industrial scale by starting from natural steroids and modifying and/or eliminating the substituents present in the steroid skeleton, introducing substituents into the steroid and/or introducing or saturating double bonds. In these reactions the 13-methyl group is left unaffected.

The 18-alkyl-estrane compounds are obtained up to now by a total synthesis whereby the steroid skeleton is built up from smaller molecules and the 18-alkyl group is built in by proper choice of the starting substances. The total synthesis is a long and laborious process particularly due to the presence of the many asymmetric carbon atoms in the steroid skeleton. It is true that many problems in connection with the synthesis have been solved by a suitable choice of the starting substances and the finding of stereospecific reactions but still many isomer-separations and purification steps are necessary owing to which the yields are low and the cost price relatively high. This might likewise be a reason why 18-alkyl-estrane compounds in spite of the promising properties and strong activities that are mentioned in literature for these compounds have found so little actual application.

The novel process for the preparation of 11β-hydroxy-18-alkyl-estrane compounds consists therein that the starting substance is an 11β-hydroxy-13-methyl-gonane compound with the partial formula I of the reaction scheme as set forth below, this steroid is reacted with an excess of an acylhypoiodite, the thus-obtained estrano-18,11β-lactone (II) is reacted with a compound RX, in which R = alkyl and X = MgBr or Li, or is hydrolysed to the 11β-hydroxy-13-carboxylic acid compound (IV) and then reacted with an alkyl lithium compound, whereafter the thus-obtained 11β-hydroxy-18-alkyl-18-ketone (III) is reduced to the 11β-hydroxy-18-alkyl-estrane compound (VI).

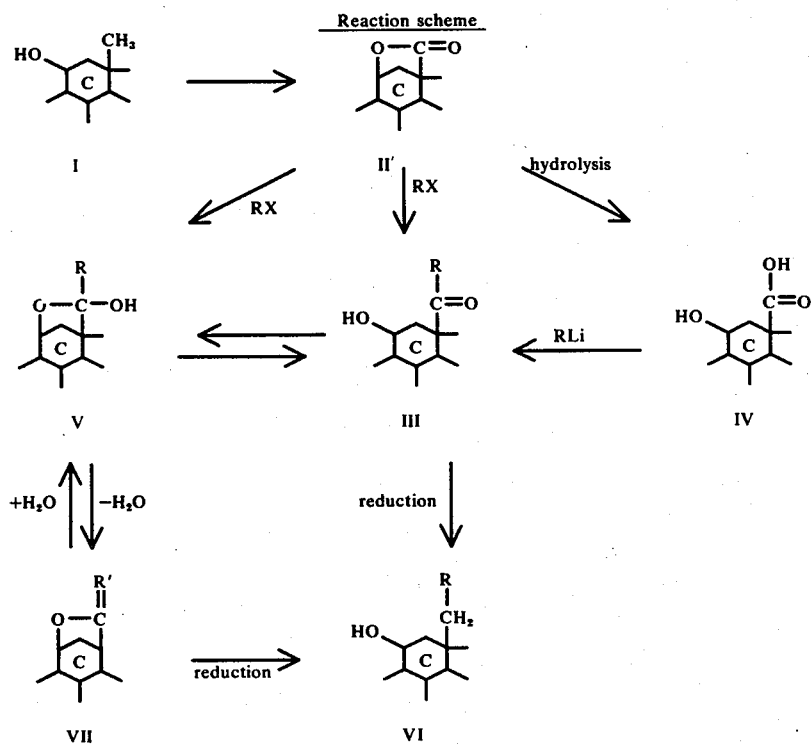

Reaction scheme

In this manner 11β-hydroxy-18-alkyl-estrane compounds can be prepared in an elegant and simple way without stereoisomeric problems and with good to excellent yields which hitherto could only be prepared along the more difficult route of total synthesis. If desired the 11β-hydroxy group can also be eliminated, for example by halogenation or sulphonylation of the hydroxyl group, followed by reductive elimination of the halogen- or sulphonyloxy group, or by oxidation of the hydroxyl group, followed by reduction of the 11-oxo group thus-obtained by the method of Wolff-Kishner. Thus, for example, 11β-hydroxy-Δ⁵-estrene-3,17-dione 3,17-diethylene ketal can be converted according to the process of the invention into 11β-hydroxy-18-methyl-Δ⁴-estrene-3,17-dione. Elimination of the 11β-hydroxy group as indicated above and introduction of a 17α-ethinyl-17β-hydroxy group by the well-known reaction of the 17-oxo group with potassium acetylide yields the important "total synthesis" compound norgestrel (= 17α-ethinyl-17β-hydroxy-18-methyl-Δ⁴-estren-3-one), which is an active progestational compound, well-known for use in oral contraceptives.

The 11β-hydroxy-18-alkyl compounds obtained in the process according to the invention are also important as starting products for pharmacologically interesting 11-substituted 18-alkyl compounds described in literature, such as the 11β,18-dimethyl-, the 11β-halogen-18-methyl-, the 11,11-methylene-18-methyl- and the 11β-methoxymethyl-18-methyl-estrane compounds. (See for example South African Pat. No. 73/9161).

The 11β-hydroxy-13-methyl-gonane compounds to be used as starting substances may have substituents in other positions in the ring system, such as oxo groups (and preferably functional derivatives thereof) in the 3 and/or 17-position; free, esterified or etherified hydroxyl groups in the 1, 2, 3, 4, 5, 6, 7, 15 and/or 16-position, of which the free hydroxyl groups are preferably protected during the process of the invention; alkyl groups such as e.g. methyl or ethyl groups in the 1, 6, 7, 9, 11α and/or 16-position; and/or a saturated or unsaturated alkyl group with 1-4 C-atoms, such as methyl, ethyl, isopropyl, viny or isopropenyl, in the 17α-position, next to a free, esterified or etherified hydroxyl group in the 17β-position. By functional derivatives of oxo groups are meant ketalised oxo-groups or oxo-groups converted into enol-derivatives thereof, such as enol ethers or enol esters. Furthermore the starting substances may possess also double bonds, for example in the 4,5-, 5,6- or 5,10 position.

Preferred starting substances are 11β-hydroxy-13-methyl-gonane compounds having the formula:

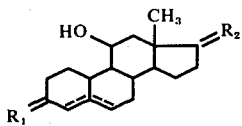

$R_1 = H_2$, $H(OR_3)$, O or ketalised O;
$R_2 = O$, ketalised O, $H(OR_4)$ or (α-alkyl)(βOR₄), the alkyl group having 1–4 C-atoms and $R_3$ and $R_4$ being H or a protecting group such as acyl or alkyl, preferably acetyl; and
a double bond is present in the position 4,5 or 5,6.

Specific examples of starting substances are: 11β-hydroxy-Δ⁵-estrene-3,17-dione 3,17-diethylene ketal, 11β,17β-dihydroxy-Δ⁵-estren-3-one 3-ethylene ketal 17-acetate, 11β-hydroxy-Δ⁴-estren-17-one 17-ethylene ketal, Δ⁴-estrene-11β,17β-diol 17-acetate, 11β-hydroxy-Δ⁴-estrene-3,17-dione, 3β,11β-dihydroxy-Δ⁵-estren-17-one 3-acetate 17-ethylene ketal 11β-hydroxy-Δ⁵-estren-17-one 17-ethylene ketal, Δ⁵-estrene-11β,17β-diol 17-acetate, 11β,17β-dihydroxy-17α-methyl-Δ⁵-estren-3-one 3-ethylene ketal 17-acetate and the corresponding 17α-ethyl compound, etc.

Known estrane compounds without 11β-hydroxy group can be easily converted into starting substances for the process according to the invention, for example by introducing in a microbiological way an 11α-hydroxyl group, using e.g. the micro-organism *Aspergillus ochraceus*, *Rhizopus nigricans* or *Pestalotia royena*, and then oxidizing the 11α-hydroxyl group, for example with chromic acid, to the 11-ketone, whereafter the 11-ketone is converted into the 11β-hydroxy-estrane compound by reduction, for example, with NaBH₄.

Thus, 19-nor-testosterone, for example, is converted into 11α-hydroxy-19-nor-testosterone via the microbiological route and last-mentioned compound is reacted with Jones' reagent to the corresponding 11,17-diketone (Δ⁴-estrene-3,11,17-trione), whereafter this 3,11,17-triketone after protection of the 3- and 17-oxo group in the form of a ketal, is converted into 11β-hydroxy-Δ⁵-estrene-3,17-dione 3,17-diketal by reduction with NaBH₄.

The 11β-hydroxy group may also be introduced directly along the microbiological route, for example with the micro-organism *Culvularia lunata*.

In accordance with the invention, an 11β-hydroxy-13-methyl-gonane compound (I) is reacted with an excess of an acylhypoiodite to give the estrano-18,11β-lactone(II). The acylhypoiodite is preferably formed in situ from iodine and an acylate from a heavy metal, such as the acetates, propionates or benzoates of the metals of the 1st, 2nd and 4th side group of the Periodic System, e.g. the silver, mercury and lead acylates. Preferably a lead tetra-acylate, for example lead tetra-acetate, is used, which forms with iodine a lead di-acylate and an acylhypoiodite. The acylhypoiodite converts the 11β-hydroxy group first into the 11β-hypoiodite group, whereafter the 11β-hydroxy-13-iodomethyl compound is formed by way of an intramolecular conversion. By the excess acylhypoiodite a repetition of the 13-substitution is effected, owing to which, probably via the 18-iodo-11β,18-epoxide or possibly via the 11β-hydroxy-18,18-diiodo compound, ultimately the estrano-18,11β-lactone (II) is formed.

The estrano-18,11β-lactone preparation is performed, for example, by dissolving or suspending the starting substance in a solvent inert with regard to the reagents, for example in a hydrocarbon, such as cyclohexane or methylcyclohexane, or in a chlorinated hydrocarbon, such as dichloromethane, carbon tetrachloride or hexachlorobutadiene, adding a lead tetra-acylate, e.g. lead tetra-acetate, and iodine and optionally a weak base, such as e.g. calcium carbonate and heating the reaction mixture while stirring. The reaction can be performed at normal or raised pressure and, for example, at the boiling temperature of the solvent while refluxing. The duration of the reaction depends i.a. on the temperature and on the solvent used. When using iodine and lead tetra-acetate in cyclohexane under reflux, the reaction will be completed within one hour as a rule. The reaction temperature is usually between 50° and 150° C.

An acceleration of the reaction can be achieved by irradiating the reaction mixture with visible and/or ultra violet light. However, preferably a radical initiator is added to the reaction mixture for that purpose. Addition of azoisobutyrodinitril, for example, turned out to favourably influence the duration of the reaction. The amount of radical initiator is not very critical. With an amount of 0.1 – 0.25 gmol per gmol steroid excellent results are obtained.

For obtaining a good yield, the amount of iodine in the reaction mixture should be such that per gmol steroid at least 1.5 gmol I₂ is present, however, usually not more than 3 gmol I₂ per gmol steroid. The amount of lead tetra-acylate expressed in gmol should at least be equal to the amount of I₂, but is preferably greater. Usually 1.5 – 5 gmol of lead tetra-acylate per gmol I₂ is employed.

The reaction time is not very critical and can be made dependent on the amount of iodine used. In proportion as the excess of $I_2$ is greater, the reaction time can be shortened.

In boiling cyclohexane and in the presence of a radical initiator, the reaction time in case of an amount of iodine of 1.5 – 2.0 gmol per gmol steroid will be between about 10 and 30 minutes.

According to the process of the invention the estrano-18,11β-lactone (II) is then reacted with a compound RX, in which R = alkyl and X = MgBr or Li. The alkyl group in the compound RX is preferably an alkyl group with 1–4 C-atoms. Examples of the compound RX are methylmagnesium bromide, methyl lithium, ethylmagnesium bromide, ethyl lithium, propylmagnesium bromide and butyl lithium.

The reaction of the estrano-18,11β-lactone with the compound RX is performed in an indifferent solvent under anhydrous conditions, for example in dry ether or dry toluene or a mixture thereof. After the reaction, the reaction mixture is gently treated with a proton-donor, such as water, diluted acid or a solution of $NH_4Cl$, water being preferred, and further processed. In this manner the 11β-hydroxy-18-alkyl-18-ketone (III) is obtained from the estrano-18,11β-lactone.

An alternative method for converting the estrano-18,11β-lactone (II) into the 11β-hydroxy-18-alkyl-18-oxo-compound (III) is the method whereby the lactone is hydrolysed first to the 11β-hydroxy-13-carboxylic acid (IV), for example by gently heating the lactone in a diluted solution of sodium hydroxide in methanol, whereafter the 11β-hydroxy-13-carboxylic acid is reacted with an alkyl lithium compound, such as e.g. methyl lithium, ethyl lithium or butyl lithium. The reaction is performed in an indifferent solvent such as e.g. tetrahydrofuran under anhydrous conditions and preferably at low temperatures, e.g. 0° C. In this manner a good yield of the 11β-hydroxy-18-alkyl-18-ketone (III) is obtained.

Finally, the 11β-hydroxy-18-alkyl-18-ketone (III) is converted into the 11β-hydroxy-18-alkyl compound (VI). The reduction of the 18-oxo group is effectively performed according to the method of Wolff-Kishner, wherein the carbonyl compound is converted into the hydrazone or semicarbazone thereof and this hydrazone or semicarbazone is decomposed under alkaline conditions. The alkaline decomposition is performed with the aid of potassium hydroxide or with an alkoxide such as e.g. sodium ethoxide. Preferably the Huang-Minlon modification is applied wherein a highly boiling solvent such as diethylene glycol, is used and the reaction is performed at a temperature about 100° C, whereby the water formed during the reaction is distilled off.

It should be noted that the 11β-hydroxy-18-alkyl-18-ketone (III) can also be present in the form of the isomeric cyclic hemi-acetal (V). It is possible therefore that the reaction of the estrano-18,11β-lactone (II) with the compound RX proceeds via the cyclic hemiacetal (V). This cyclic hemi-acetal (V) and thus the 11β-hydroxy-18-alkyl-18-ketone (III) can easily be dehydrated, such as e.g. with the aid of silicagel, to the 18,18-alkylidene-11β,18-oxido-compound (VII). This last-mentioned compound can be reduced to the 11β-hydroxy-18-alkyl compound (VI) in the same manner as the 11β-hydroxy-18-alkyl-18-ketone. The reduction of the 11β-hydroxy-18-alkyl-18-ketone (III) to the 11β-hydroxy-18-alkyl compound ought to be considered therefore as an equivalent of the dehydration of the 11β-hydroxy-18-alkyl-18-ketone (III), followed by the reduction of the 18,18-alkylidene-11β,18-oxido-compound (VII).

In the process according to the invention, vulnerable oxo- and/or hydroxy groups present in the steroid are preferably protected temporarily; an oxo group, for example, in the form of its ketal and a hydroxy group in the form of an ether or an ester, wherby the protection in the form of an ester is usually preferred.

Thus, for example, when the starting substance is 11β-hydroxy-Δ⁴-estrene-3,17-dione, this dione is first converted into the 11β-hydroxy-Δ⁵-estrene-3,17-dione 3,17-diethylene ketal, whereafter this diethylene ketal is converted in the first reaction step with an excess of an acylhypoiodite into 3,17-dioxo-Δ⁵-estreno-18,11β-lactone 3,17-diethylene ketal. This lactone is then converted into 11β-hydroxy-18-methyl-Δ⁵-estrene-3,17,18-trione 3,17-diethylene ketal, for example with methyl magnesium bromide or methyl lithium, said ketal then being reduced according to the method of Wolff-Kishner to 11β-hydroxy-18-methyl-Δ⁵-estrene-3,17-dione 3,17-diethylene ketal. After removal of the protecting ketal groups by hydrolysis and elimination of the 11β-hydroxy group in the manner as described before, 18-methyl-Δ⁴-estrene-3,17-dione is obtained which after ethynylation of the 17-oxo group, e.g. with potassium acetylide, yields the known compound norgestrel (= 17α-ethynyl-17β-hydroxy-18-methyl-Δ⁴-estrene-3-one).

The intermediates obtained in the process according to the invention, to wit the estrano-18,11β-lactones and the 11β-hydroxy-18-alkyl-18-ketones of the estrane series, are novel. The invention therefore also relates to novel intermediates of the general formula:

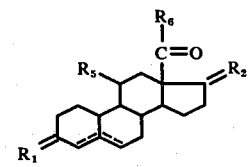

wherein $R_1$ and $R_2$ have the meanings as given hereinbefore;

$R_5$ = a free, esterified or etherified hydroxyl group;

$R_6$ = alkyl (1-4 C) or $R_5$ and $R_6$ together from epoxy; and a double bond is present in the 4,5- or 5,6-position.

An ester group that may be present is derived from an organic carboxylic acid with 1–18 C-atoms. This ester group is preferably introduced after the introduction of the 18,11β-lactone group or the 18-alkyl-18-oxo-group. An ether group that may be present can be, for example, the methylether-, the ethylether-, the tetrahydropyranylether- or the trimethylsilylether-group. A ketal group that may be present can be, for example, the ethylene ketal or dimethyl ketal group.

These novel intermediates are not only of importance for the preparation of pharmacologically important 18-alkyl-estrane compounds therefrom, but also possess interesting oestrogenic, progestative, ovulation-inhibiting and peripheric antifertility properties.

The invention is further illustrated with the following examples:

Example I

A 10 litre three-necked flask was successively filled with 4.1 l of cyclohexane, 111.6 g of lead tetra-acetate, 37.2 g of calcium carbonate and 22.8 g of iodine. The mixture was refluxed for 10 minutes. To the boiling reaction mixture a suspension of 22.8 g of 11$\beta$-hydroxy-$\Delta^5$-estrene-3,17-dione 3,17-diethylene ketal and 2.04 g of azoisobutyrodinitril in 600 ml of cyclohexane was added as quickly as possible. Then the mixture was refluxed for 25 minutes. After that the reaction mixture was cooled down and the precipitate filtered off. The filtrate was washed with 2.5 l of water in which 50 g of sodium thiosulphate had been dissolved, and then washed with water to neutral. The organic layer was dried on sodium sulphate, filtered and evaporated to dryness. The foamy residue obtained was chromatographed on silicagel with toluene/ethyl acetate 1/1. Crystallisation of the correct fractions gave 13.6 g of 3,17-dioxo-$\Delta^5$-estreno-18,11$\beta$-lactone 3,17-diethylene ketal, m.p. 163°–164.5° C.

In a similar manner 11$\beta$,17$\beta$-dihydroxy-$\Delta^5$-estren-3-one 3-ethylene ketal and 11$\beta$,17$\beta$-dihydroxy-17$\alpha$-methyl-$\Delta^5$-estren-3-one 3-ethylene ketal 17-acetate were converted into the corresponding 18,11$\beta$-lactones.

EXAMPLE II 11.16 g of lead tetra-acetone and 3.7 g of calciumcarbonate were suspended in 420 ml of dry cyclohexane. To this suspension were added 2.28 g of iodine.

After refluxing the mixture for 10 minutes, a suspension of 1.9 g of $\Delta^4$-estrene-11$\beta$,17$\beta$-diol 17$\beta$-acetate and 0.2 g of azoisobutyrodinitril in 40 ml of dry cyclohexane was added, whereafter the reaction mixture was refluxed for another 35 minutes. The reaction mixture was cooled to room temperature and filtered on hyflo. The filtrate was washed with a 5% solution of sodium thiosulphate and after that with water. After drying on sodium sulphate, the organic layer was concentrated in vacuo yielding an oily residue of 3.7 g.

After chromatography on silicagel with toluene/ethylacetate 9/1 and after crystallisation of the correct fractions, 0.95 g of 17$\beta$-hydroxy-$\Delta^4$-estreno-18,11$\beta$-lactone 17$\beta$-acetate were obtained; melting point: 157°–159° C.

In a similar manner $\Delta^5$-estrene-11$\beta$,17$\beta$-diol 17$\beta$-acetate, 11$\beta$-hydroxy-$\Delta^5$-estren-17-one 17-ethylene ketal and 17$\alpha$-ethyl-$\Delta^4$-estrene-11$\beta$,17$\beta$-diol 17$\beta$-acetate were converted into the corresponding 18,11$\beta$-lactones.

EXAMPLE III 3.8 g of magnesium turnings were suspended in 280 ml of ether. Methyl bromide was added until all the magnesium was dissolved. After cooling to room temperature, a solution of 22.2 g of 3,17-dioxo-$\Delta^5$-estreno-18,11$\beta$-lactone 3,17-diethylene ketal in 420 ml of dry toluene was added. The reaction mixture was stirred for one hour at room temperature, after that carefully decomposed with 400 ml of 0.4 N HCl and poured out into 2.8 l of water. Extraction with methylene chloride yielded an organic layer that was washed to neutral with water, dried on sodium sulphate, filtered and evaporated in vacuo to dryness. 19.5 g of 11$\beta$-hydroxy-18-methyl-$\Delta^5$-estrene-3,17,18-trione 3,17-diethylene ketal were obtained with a melting point of 175°–178° C.

In a similar manner the 18,11$\beta$-lactones, obtained in the Examples I and II, were converted into the corresponding 11$\beta$-hydroxy-18-methyl-18-ketones.

By taking ethylmagnesium bromide instead of methylmagnesium bromide the corresponding 18-ethyl-18-ketones were obtained. With butyl lithium the corresponding 18-butyl-18-ketones were obtained.

EXAMPLE IV a. 7.5 g of crude 3,17-dioxo-$\Delta^5$-estreno-18,11$\beta$-lactone 3,17-diethylene ketal were dissolved in 50 ml of methanol. To this solution 20 ml of 10% sodium hydroxide solution were added whereafter the mixture was stirred for 1.5 hours at 50° C. After that the mixture was poured out into 750 ml of water. Neutralisation to pH = 7 was effected with 2N HCl. Extraction with ethyl acetate, drying of the extract on sodium sulphate, filtration and evaporation of the extract to dryness yielded 4.2 g of 11$\beta$-hydroxy-3,17-dioxo-$\Delta^5$-estrene-13-carboxylic acid 3,17-diethylene ketal.

b. 1.21 g of 11$\beta$-hydroxy-3,17-dioxo-$\Delta^5$-estrene-13-carboxylic acid 3,17-diethylene ketal were dissolved in 20 ml of tetrahydrofurane. After cooling down to 0° C, 6 ml of 1.5 M methyl lithium were slowly added to this solution at this temperature and after that the solution was stirred for 1 hour at 0° C. Pouring out into 200 ml of ice water, extraction with methylene chloride, drying of the extract on sodium sulphate, filtration and evaporation in vacuo of the extract yielded a residue, from which by chromatography on silica (toluene/ethyl acetate 1/1), 0.48 g of 11$\beta$-hydroxy-18-methyl-$\Delta^5$-estrene-3,17,18-trione 3,17-diethylene ketal were obtained with a melting point of 175°–178° C.

EXAMPLE V 10.2 g of 11$\beta$-hydroxy-18-methyl-$\Delta^5$-estrene-3,17,18-trione 3,17-diethylene ketal were suspended in 97 ml of 100% ethanol, after which 233 ml of diethylene glycol, 97 ml of hydrazine-hydrate and 20.4 g of hydrazine-dihydro-chloride were added.

The reaction mixture was kept at 100° C for 7 hours whereafter 37 g of powdered potassium hydroxide and 713 ml of diethylene glycol were added.

The reaction mixture was then brought at 180° C while simultaneously distilling off the lower boiling fractions and keeping the mixture at 180° C for 4.5 hours. After that the mixture was cooled down to room temperature and poured out into 7 l of ice water. The mixture was neutralised with 18% HCl. The crystals were filtered off, washed with water and dried at 70° C in vacuo. The crystals were recrystallised from ethyl acetate.

In this manner 8.45 g of 11$\beta$-hydroxy-18-methyl-$\Delta^5$-estrene-3,17-dione 3,17-diethylene ketal were obtained with a melting point of 176°–179° C.

In a similar manner the other 11$\beta$-hydroxy-18-alkyl-18-ketones mentioned in Example III were reduced to the corresponding 11$\beta$-hyroxy-18-alkyl compounds.

EXAMPLE VI a. 6.7 g of 11$\beta$-hydroxy-18-methyl-$\Delta^5$-estrene-3,17,18-trione 3,17-diethylene ketal were dissolved in 220 ml of tolune/ethyl acetate 1/1, whereafter 67 g of silicagel were added to the solution. After stirring for 16 hours at room ternperature the silicagel was filtered off and washed out well with toluene/ethyl acetate. The filtrate was evaporated to dryness. Yield: 6.1 g of 11β,18-epoxy-18,18-methylene-Δ⁵-estrene-3,17-dione 3,17-diethylene ketal, m.p. 152°–155° C.

b. 3.15 g of 11β,18-epoxy-18,18-methylene-Δ⁵-estrene-3,17-dione 3,17-diethylene ketal were suspended in 30 ml of 100% ethanol. To the suspension were added: 72 ml of diethylene glycol, 29 ml of hydrazine hydrate and 6.3 g of hydrazine-dihydro-chloride. The reaction mixture was kept at 100° C for 7 hours and after that 11.4 g of powdered potassium hydroxide and 220 ml of diethylene glycol were added. The reaction mixture was brought at 200° C while distilling off the lower boiling fractions and was kept at 200° C for 1.5 hours. The reaction mixture was cooled down to room temperature and poured out into 2 l of water. The mixture was neutralised with 18% HCl, stirred for one hour, after which the crystals were filtered off, washed with water and dried at 70° C in vacuo. Recrystallisation from ethyl acetate yielded 1.1 g of 11β-hydroxy-18-methyl-Δ⁵-estrene-3,17-dione 3,17-diethylene ketal with a melting point of 177°–179.5° C.

EXAMPLE VII

To a suspension of 9.54 g lead tetra-acetate and 3.18 g calcium carbonate in 356 ml cyclohexane 1.95 g iodine were added. The mixture was refluxed for 10 minutes. To the boiling mixture a suspension of 1.95 g 11β-hydroxy-estrane-3,17-dione 3,17-diethylene ketal and 0.174 g azoisobutyrodinitrile in 100 ml cyclohexane was added, whereafter the reaction mixture was refluxed for 30 minutes.

After cooling the reaction mixture to room temperature it was filtered on hyflo. The filtrate was washed with an aqueous solution (5%) of sodium thiosulphate and then with water. The organic layer was dired on sodium sulphate and evaporated in vacuum, yielding a dry residue of 3.7 g. Chromatography on silicagel with tolune/ethyl acetate 6/4 gave 3,17-dioxo-estrano-18, 11β-lactone 3,17-diethylene ketal.

We claim:

1. Process for the preparation of an 11β-hydroxy-18-alkyl steroid of the estrane series, the alkyl having 1 to 4 carbon atoms, which steroid may be substituted in the 3- and/or 17-position by an oxo group or a functional derivative thereof, in the 1, 2, 3, 4, 5, 6, 7, 15 and/or 16-position by hydroxy, acyloxy derived from an organic carboxylic acid having 1–18 carbon atoms, alkoxy having 1–2 carbon atoms, tetrahydropyranyloxy or trimethylsilyloxy in the 1, 6, 7, 9, 11α and/or 16-position with alkyl having 1–2 carbon atoms and in the 17α-position with saturated or unsaturated alkyl having 1–4 carbon atoms next to hydroxy, acyloxy derived from an organic carboxylic acid having 1–18 carbon atoms, alkoxy having 1–2 carbon atoms, tetrahydropyranyloxy or trimethylsilyloxy in 17β-position, and which may have a double bond in the 4,5-, 5,6-, or 5,10-position, which comprises reacting the corresponding 11β-hydroxy-13-methyl-gonane compound with an excess of an acyl hypoiodite and reacting the thus-obtained estrano-18, 11β-lactone with a compound RX, in which R = alkyl and X = MgBr or Li and thereafter reducing the thus-obtained 11β-hydroxy-18-alkyl-18-ketone to the 11β-hydroxy-18-alkyl-steroid of the estrane series.

2. Process according to claim 1, in which the starting 11β-hydroxy-13-methyl-gonane compound has the formula

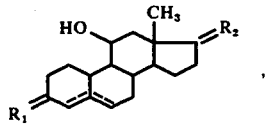

$R_1 = H_2$, $H(OR_3)$, O or ketalised O;
$R_2 = $ O, ketalised O, $H(OR_4)$ or (α-alkyl)(βOR₄), the alkyl group having 1–4 C-atoms and $R_3$ and $R_4$ being H or a protecting group such as acyl or alkyl; and a double bond is present in the 4,5- or 5,6-position.

3. Process according to claim 2, in which in the formula $R_1 = H_2$, H(Oacetyl) or ethylenedioxy;
$R_2 = $ ethylenedioxy, αH(βOacetyl) or (α-alkyl 1–4 C) (βOacetyl); and a double bond is present in the 4,5- or 5,6-position.

4. Process according to claim 1 in which the acyl-hypoiodite is formed in situ from iodine and an acylate of a heavy metal of Group IB, Group IIB and Group IVB of the Periodic System.

5. Process according to claim 4, in which lead tetra acetate is used as acylate of said heavy metal.

6. Process according to claim 4, in which per gmol steroid 1.5–3.0 gmol iodine are used and at least an equivalent amount of lead tetra-acylate.

7. Process according to claim 6, in which per gmol iodine 1.5–5 gmol of lead tetra-acylate are used.

8. Process according to claim 1, in which in the first step a cyclic hydrocarbon is used as solvent.

9. Process according to claim 8, in which cyclohexane is used as solvent.

10. Process according to claim 1, in which in the first step the reaction is performed in the presence of a radical initiator.

11. Process according to claim 10, in which azoisobutyrodinitril is used as radical initiator.

12. Process according to claim 10, in which 0.1–0.25 gmol radical initiator is used per gmol steroid.

13. Process according to claim 1, in which in the compound RX the alkyl group has 1–4 carbon atoms.

14. Process according to claim 1, in which the reaction of the estrano-18,11β-lactone with the compound RX is performed in an indifferent solvent under anhydrous conditions.

15. Process according to claim 1, in which the reaction of the alkyl lithium compound with the 11β-hydroxy-13-carboxylic acid is performed in an indifferent solvent under anhydrous conditions and at low temperatures.

16. Process according to claim 1, in which the 18-oxo group in the 11β-hydroxy-18-alkyl-18-ketone is reduced by reacting the 18-ketone with a hydrazine or a semicarbazide and decomposing the hydrazone or semicarbazone thus obtained with the aid of potassium hydroxide or an alkoxide.

17. Process according to claim 16, in which the reduction is performed in boiling diethylene glycol, whereby the water formed during the reaction is distilled off.

18. A compound having the formula

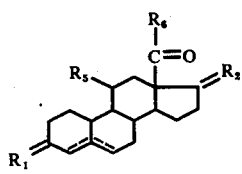

- $R_1 = H_2$, $H(OR_3)$, O or ketalised O;
- $R_2 = O$, ketalised O, $H(OR_4)$ or ($\alpha$-alkyl)($\beta OR_4$) the alkyl group having 1–4 carbon atoms and $R_3$ and $R_4$ being H or a protecting group such as acyl or alkyl;
- $R_5 =$ OH, acyloxy derived from an organic carboxylic acid having 1–18 carbon atoms, alkoxy having 1–2 carbon atoms, tetrahydropyranyloxy or trimethylsilyloxy;
- $R_6 =$ alkyl having 1–4 carbon atoms or $R_5$ and $R_6$ together form epoxy; and a double bond is present in the 4,5- or 5,6-position.

19. A compound according to claim 18, wherein
- $R_1 = H_2$ or ethylenedioxy;
- $R_2 =$ ethylenedioxy or $\alpha H(\beta Oacetyl)$;
- $R_5 =$ OH;
- $R_6 =$ methyl or $R_5$ and $R_6$ together form epoxy; and a double bond is present in the 4,5- or 5,6-position.

20. Process for the preparation of an 11$\beta$-hydroxy-18-alkyl streoid of the estrane series, the alkyl having 1 to 4 carbon atoms, which steroid may be substituted in the 3- and/or 17-position by an oxo group or a functional derivative thereof, in the 1, 2, 3, 4, 5, 6, 7, 15 and/or 16-position by hydroxy, acyloxy derived from an organic carboxylic acid having 1–18 carbon atoms, alkoxy having 1–2 carbon atoms, tetrahydropyranyloxy or trimethylsilyloxy in the 1, 6, 7, 9, 11$\alpha$ and/or 16-position with alkyl having 1–2 carbon atoms and in the 17$\alpha$-position with saturated or unsaturated alkyl having 1–4 carbon atoms next to hydroxy, acyloxy derived from an organic carboxylic acid having 1–18 carbon atoms, alkoxy having 1–2 carbon atoms, tetrahydropyranyloxy or trimethylsilyloxy in 17$\beta$-position, and which may have a double bond in the 4,5-, 5,6-, or 5,10-position, which comprises reacting the corresponding 11$\beta$-hydroxy-13-methyl-gonane compound with an excess of an acyl hypoiodite, hydrolyzing the thus-obtained estrano-18, 11$\beta$-lactone to the corresponding 11$\beta$-hydroxy-13-carboxylic acid, then reacting said carboxylic acid with an alkyl lithium compound, and thereafter reducing the thus-obtained 11$\beta$-hydroxy-18-alkyl-18-ketone to the 11$\beta$-hydroxy-18-alkyl-steroid of the estrane series.

21. Process according to claim 20 in which the starting 11$\beta$-hydroxy-13-methyl-gonane compound has the formula

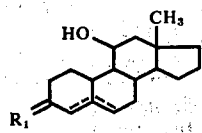

wherein
- $R_1 = H_2$, $H(OR_3)$, O or ketalised O;
- $R_2 = O$, ketalised O, $H(OR_4)$ or ($\alpha$-alkyl)($\beta OR_4$), the alkyl group having 1–4 C-atoms and $R_3$ and $R_4$ being H or a protecting group such as acyl or alkyl; and a double bond is present in the 4,5- or 5,6-position.

22. Process according to claim 21 in which in the formula
- $R_1 = H_2$, H(Oacetyl) or ethylenedioxy;
- $R_2 =$ ethylenedioxy, $\alpha H(\beta Oacetyl)$ or ($\alpha$-alkyl 1–4 C) ($\beta Oacetyl$); and a double bond is present in the 4,5- or 5,6-position.

23. Process according to claim 20 in whcih the acyl hypoiodite is formed in situ from iodine and an acylate or a heavy metal of Group IB, Group IIB and Group IVB of the Periodic System.

24. Process according to claim 23 in which lead tetra acetate is used as acylate of said heavy metal.

25. Process according to claim 23, in which per g mol steroid 1.5–3.0 g mol iodine are used and at least an equivalent amount of lead tetra-acylate.

26. Process according to claim 25, in which per g mol iodine 1.5–5 g mol of lead tetra-acylate are used.

27. Process according to claim 20, in which in the first step a cyclic hydrocarbon is used as solvent.

28. Process according to claim 27, in which cyclohexane is used as solvent.

29. Process according to claim 20, in which in the first step the reaction is performed in the presence of a radical initiator.

30. Process according to claim 29, in which azoisobutyrodinitrile is used as radical initiator.

31. Process according to claim 29, in which 0.1–0.25 g mol radical initiator is used per g mol steroid.

32. Process according to claim 20, in which in said alkyl lithium compound the alkyl group has 1–4 carbon atoms.

33. Process according to claim 20, in which the 18-oxo group in the 11$\beta$-hydroxyl-18-alkyl-18-ketone is reduced by reacting the 18-ketone with a hydrazine or a semicarbazide and decomposing the hydrazone or semicarbazone thus obtained with the aid of potassium hydroxide or an alkoxide.

34. Process according to claim 33, in which the reduction is performed in boiling diethylene glycol, whereby the water formed during the reaction is distilled off.

* * * * *

UNITED STATES PATENT AND TRADEMARK OFFICE
CERTIFICATE OF CORRECTION

PATENT NO. : 4,031,074
DATED : June 21, 1977
INVENTOR(S) : Hendrik Paul deJongh and Cornelis Wilhelmus van Bokhoven It is certified that error appears in the above-identified patent and that said Letters Patent are hereby corrected as shown below:

Column 3, line 26, "viny" should read -- vinyl --; after the comma following the formula between lines 36 to 40, there should be inserted -- wherein --.

Column 5, line 52, "about" should read -- above --.

Column 7, line 4, "4.1" should read -- 4.2 --.

Column 9, line 66, insert -- wherein -- after the comma.

Column 11, line 6, insert -- wherein -- after the comma; line 28, "streoid" should read -- steroid --.

Column 12, line 21, "whcih" should read -- which --.

Signed and Sealed this

Twentieth Day of December 1977

[SEAL]

Attest:

RUTH C. MASON
Attesting Officer

LUTRELLE F. PARKER
Acting Commissioner of Patents and Trademarks